(12) United States Patent
Kalyanaraman et al.

(10) Patent No.: US 7,223,864 B2
(45) Date of Patent: May 29, 2007

(54) 2-HYDROXYETHIDIUM, METHODS OF PREPARATION AND USES THEREOF

(75) Inventors: Balaraman Kalyanaraman, Wauwatosa, WI (US); Hongtao Zhao, Milwaukee, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 356 days.

(21) Appl. No.: 10/820,599

(22) Filed: Apr. 8, 2004

(65) Prior Publication Data

US 2005/0227307 A1    Oct. 13, 2005

(51) Int. Cl.
 *C07D 221/06* (2006.01)
 *C07D 221/18* (2006.01)
 *C12Q 1/00* (2006.01)
(52) U.S. Cl. ............... 546/79; 435/4; 546/26
(58) Field of Classification Search ............ 435/26, 435/4
 See application file for complete search history.

(56) References Cited

U.S. PATENT DOCUMENTS

2002/0081711 A1* 6/2002 Herlyn et al. ............ 435/235.1

OTHER PUBLICATIONS

Zhao et al, Free Radical Biology & Medicine, vol. 34, No. 11, pp. 1359-1368 (2003).*
Zielonka et al, Free Radical Biology & Medicine, vol. 39, No. 7, pp. 853-863, (Oct. 2005).*
Zhao et al, PNAS, vol. 102, No. 16, pp. 5727-5732, (Apr. 19, 2005).*
Budd et al, FEBS Letters, V. 415, pp. 21-24, (1997).*
Georgiou et al, "An ultrasensitive fluorescent assay for the in vivo quantification of superoxide radical in organisms," (Analytical Chemistry), Dec. 1, 2005, vol. 347, p. 144-151.*
B. Fink, A. Doughan, D. Harrison, S. Dikalov, "Measurements of intracellular superoxide in endothelial cells and aortas using dihydroethidium and new HPLC-based assay," Free Radical Biology and Medicine, vol. 35, Supplement 1, p. S144.
H. Zhao, S. Kalivendi, H. Zhang, J. Joseph, K. Nithipatikom, J. Vasquez-Vivar, & B. Kalyanaraman, "Superoxide reacts with hydroethidine but forms a fluorescent product that is distinctly different from ethidium: potential implications in intracellular fluorescence detection of superoxide," Free Radical Biology and Medicine, vol. 34, No. 11, pp. 1359-1368, 2003.
F.C. Luft, "Genetics, etiology, and pathogenesis of hypertension, vascular injury, and renal diseases," http://www.mdc-berlin.de/englisch/research/research_areas/cardiovascular/luft.htm.

* cited by examiner

*Primary Examiner*—Christopher R. Tate
*Assistant Examiner*—Amanda P. Wood
(74) *Attorney, Agent, or Firm*—Quarles & Brady LLP

(57) ABSTRACT

The inventors have purified the fluorescent product in the hydroethidine-based supeorxide detection assays and further identified the product as 2-hydroxyethidium. Methods for synthesizing 2-hydroxyethidium and for detecting and quantifying superoxide are provided.

25 Claims, 12 Drawing Sheets

Hydroethidine

Ethidium 2-hydroxyethidium

2-HYDROXYETHIDIUM, METHODS OF PREPARATION AND USES THEREOF

STATEMENT REGARDING FEDERALLY SPONSORED RESEARCH OR DEVELOPMENT

This invention was made with United States government support awarded by the following agency: NIH HL073056 and 1PIHL68769-01. The United States has certain rights in this invention.

CROSS-REFERENCE TO RELATED APPLICATIONS

Not applicable.

BACKGROUND OF THE INVENTION

One of the most popular assays for detecting superoxide in cells and tissues involves the use of fluorescence-based techniques (Rothe, G. and Valet G. *J. Leukoc. Biol.* 47:440–448, 1990; Carter, W. et al. *J. Leukoc. Biol.* 55:253–258, 1994; Bindokas, V. et al. *J. Neurosci.* 16:1324–1336, 1996; Budd, S. et al. *FEBS Lett.* 415:21–24, 1997; Castilho, R. et al. *J. Neurochem.* 72:1394–1401, 1999; and Suzuki, H. et al. *Hypertension* 25:1083–1089, 1995). Generally, the red fluorescence arising from oxidation of hydroethidine (HE) (also called dihydroethidium (DHE), FIG. 1) is detected (Nakane, H. et al. *Hypertension* 35:595–601, 2000; Miller, F. et al. *Circ. Res.* 82:1298–1305, 1998; Kawase, M. et al. *Stroke* 30:1962–1968, 1999; Kim, G. et al. *Stroke* 33:809–815, 2002; Sorescu, D. et al. *Circulation* 105:1429–1435, 2002; Dantas, A. P. et al. *Hypertension* 39:405–411, 2002; Paravicini, T. et al. *Circ. Res.* 91:54–61, 2002; and Luo, J. et al. *J. Neurosci. Meth.* 120:105–112, 2002). HE is synthesized from sodium borohydride reduction of ethidium ($E^+$), a two-electron oxidation product (Thomas, G. and Roques, B. *FEBS Lett.* 26:169–175, 1972). It is the common belief in the art that the reaction between superoxide and HE results in the formation of a two-electron oxidized product, $E^+$, that binds to DNA and leads to the enhancement of red fluorescence (excitation, 500–530 nm; emission, 590–620 nm). Most previous fluorescence measurements have been performed using a kinetic mode and typically acquired at a single wavelength corresponding to that of $E^+$ (Schuchmann, S. and Heinemann, U. *Free Radic. Biol. Med.* 28:235–250, 2000; Zou, A.-P. et al. *Hypertension* 37:547–553, 2001; Kevin, L. et al. *Am. J. Physiol. Heart Circ. Physiol.* 284: H566–H574, 2003; Benov, L. et al. *Free Radic. Biol. Med.* 25:826–831, 1998; and Vanden Hoek, T. et al. *J. Mol. Cell Cardiol.* 29:2571–2583, 1997). Alternatively, the red fluorescence due to oxidized HE was visualized in cells and tissues using fluorescence or confocal microscopy. This red fluorescence, often referred to as the "$E^+$ fluorescence," is inhibited by intracellular superoxide dismutase and other superoxide scavengers (Nakane, H. et al. *Hypertension* 35:595–601, 2000; Miller, F. et al. *Circ. Res.* 82:1298–1305, 1998; Kawase, M. et al. *Stroke* 30:1962–1968, 1999; Kim, G. et al. *Stroke* 33:809–815, 2002; Sorescu, D. et al. *Circulation* 105:1429–1435, 2002; Dantas, A. P. et al. *Hypertension* 39:405–411, 2002; Paravicini, T. et al. *Circ. Res.* 91:54–61, 2002; and Luo, J. et al. *J. Neurosci. Meth.* 120:105–112, 2002).

To the inventors' knowledge, the question of whether superoxide-dependent oxidation of HE actually generates $E^+$ as a product has never been definitively answered. The answer to this question is important for the accurate detection and quantitation of superoxide through the use of HE.

BRIEF SUMMARY OF THE INVENTION

The present invention is summarized in that the inventors have discovered that the fluorescent product generated by the oxidization of HE by superoxide in supeorxide detection assays is 2-hydroxyethidium. The identification of 2-hydroxyethidium as the reaction product is a surprise because it contradicts the common belief in the art that the reaction product was $E^+$.

In one aspect, the present invention relates to a substantially purified 2-hydroxyethidium. In other aspects, the present invention relates to methods for synthesizing 2-hydroxyethidium and for detecting and quantifying superoxide in various samples.

DETAILED DESCRIPTION OF THE INVENTION

Figure 1:
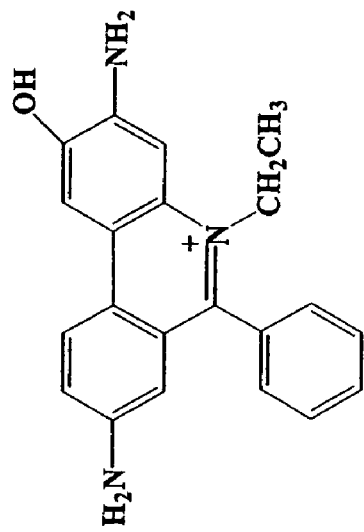
FIG. 1 shows chemical structures of HE, $E^+$ and 2-hydroxyethidium.
Figure 1:
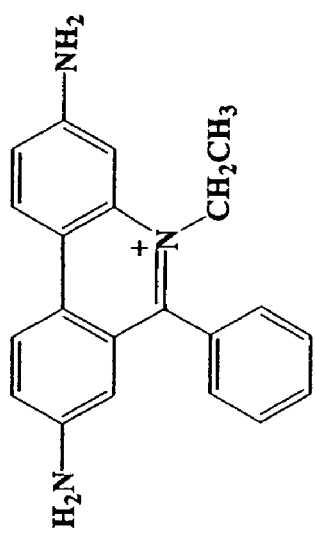
Figure 1:
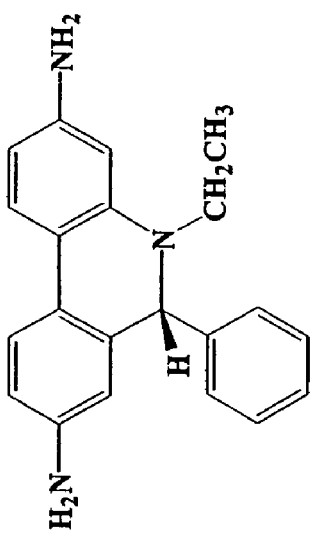

It is disclosed here that when HE is added to a sample that contains superoxide, HE is oxidized to 2-hydroxyethidium rather than the commonly believed E$^+$. As shown in the examples below, the inventors have purified the reaction product between HE and superoxide using HPLC and identified the product as 2-hydroxyethidium using LCQ-MS, MS/MS and NMR. The definitive identification of the reaction product between HE and superoxide provides more accurate tools for superoxide detection and quantitation. A cost effective method for synthesizing and purifying 2-hydroxyethidium is also disclosed.

In one aspect, the present invention relates to substantially purified 2-hydroxyethidium. Although 2-hydroxyethidium was inherently produced when HE-based prior art superoxide detection methods were practiced, 2-hydroxyethidium had never been substantially purified prior to the present invention. By "substantially purified," we mean a 2-hydroxyethidium-containing composition at least 80% (by weight) of which (80% pure), preferably at least 85% or 90% (by weight) of which (85% or 90% pure), more preferably at least 95% or 97% (by weight) of which (95% or 97% pure), and most preferably at least 99% or 99.5% (by weight) of which (99% or 99.5% pure) is 2-hydroxyethidium.

In another aspect, the present invention relates to a method for detecting superoxide in a sample. The method involves adding HE to the sample, subjecting the sample to conditions under which HE and superoxide react to generate 2-hydroxyethidium, and detecting specifically the presence of 2-hydroxyethidium in the sample wherein the presence of 2-hydroxyethidium indicates the presence of superoxide in the sample. By "detecting specifically the presence of 2-hydroxyethidium," we mean that the detection method employed detects signals from 2-hydroxyethidium without substantial interference by signals from E$^+$ when E$^+$ is present in equal molar amount with 2-hydroxyethidium. The interference of E$^+$ signal is not substantial if less than 10%, preferably less than 5% or 3%, and more preferably less than 1% or 0.5% of the total signal detected is originated from E$^+$. With the disclosure of 2-hydroxyethidium as well as various characteristics of 2-hydroxyethidium versus E$^+$ such as their fluorescence spectra, a skilled artisan can readily detect 2-hydroxyethidium specifically, using a variety of methods with which the skilled artisan is familiar. As an example, a HPLC-based method for specifically detecting 2-hydroxyethidium is described in the examples below.

In another aspect, the present invention relates to a method for determining the amount of superoxide in a sample. The method involves adding HE to the sample, subjecting the sample to conditions under which HE and superoxide react to form 2-hydroxyethidium, measuring specifically the amount of 2-hydroxyethidium in the sample in order to determine the amount of superoxide in the sample. By "measuring specifically the amount of 2-hydroxyethidium," we mean that the measuring method detects signals from 2-hydroxyethidium without substantial interference by signals from E$^+$ when E$^+$ is present in equal molar amount with 2-hydroxyethidium. The interference of E$^+$ signal is not substantial if less than 10%, preferably less than 5% or 3%, and more preferably less than 1% or 0.5% of the total signal detected is originated from E$^+$.

The detection and quantitation methods described above are not limited to any particular sample containing or suspected of containing superoxide. In one embodiment, the methods are practiced with a biological sample. By "biological sample," we mean a cell, tissue or fluid sample from an animal (including human and non-human animals) or plant, a sample from cultured cells or a culture medium, a microorganism sample (e.g., yeasts, bacteria and fungi samples), or a preparation derived from any of the foregoing. All known HE-based fluorescence methods for detecting superoxide in biological samples can be practiced with the present invention by employing the 2-hydroxyethidium specific detection and quantitation methods disclosed herein.

The detection and quantitation methods described above can also be used as tools for diagnosing and monitoring the progression of diseases and conditions involving abnormal superoxide levels in one or more body tissues. Drug testing and screening methods for these diseases and conditions are also enabled by the present invention. For example, superoxide can act as a potent vasoconstrictor and elevated level of superoxide production has been associated with hypertension. One can measure the superoxide level in the blood for diagnosing purposes and for monitoring the progression of hypertension as well as hypertension-related diseases and conditions. In testing and screening drugs for diseases and conditions involving abnormal superoxide levels, the effect of an agent (e.g., an antioxidant) on the superoxide level of a relevant body tissue is determined by the methods of the present invention. In the case of hypertension and related diseases and conditions, agents that can reduce the level of superoxide are drug candidates. Various hypertension animal models such as the one described in Cuzzocrea S. et al., FASEB J. 18: 94–101, 2004 (incorporated herein by reference in its entirety) can be used in connection with the methods of the present invention for hypertension drug testing and screening.

The conditions under which HE and superoxide can react to form 2-hydroxyethidium are known in the art. For example, the conditions of all known HE-based fluorescence methods for detecting superoxide are suitable conditions for HE and superoxide to form 2-hydroxyethidium. In addition, a skilled artisan can readily determine whether a particular set of conditions are suitable for 2-hydroxyethidium formation by exposing HE and superoxide to the set of conditions and determining whether 2-hydroxyethidium forms as a result (e.g., by the HPLC-based method described in the examples) wherein the formation of 2-hydroxyethidium indicates that the set of conditions are suitable for 2-hydroxyethidium formation.

In another aspect, the present invention relates to a method for obtaining substantially purified 2-hydroxyethidium. The method involves mixing superoxide and HE under conditions suitable for superoxide and HE to form 2-hydroxyethidium. Substantially purified 2-hydroxyethidium is then obtained by purifying the compound from the reaction mixture, which can be readily accomplished by a skilled artisan using any purification method with which the skilled artisan is familiar.

In another aspect, the present invention relates to yet another method for synthesizing and purifying 2-hydroxyethidium. In this method, Fremy's salt is first dissolved in a first solution containing acetonitrile and phosphate buffer to form a Fremy's salt solution. The acetonitrile and phosphate buffer in the first solution are preferably of about equal volume (about 1 to 1 volume ratio). The phosphate buffer is preferably of about 10 mM to about 50 mM and has a pH of about 7.4 to about 7.6. The Fremy's salt solution is then mixed with a second solution containing HE and phosphate buffer so that Fremy's salt and HE react to form 2-hydroxyethidium. Preferably, the phosphate buffer of the second solution is of about 50 mM to about 100 mM and has a pH of about 7.4 to about 7.6. The HE concentration in the second solution is preferably from about 60 µM to about 120 µM. For optimal conversion efficiency, the molar ratio of Fremy's salt to HE in the reaction mixture is about 4.5 to 1 although other ratios can also work. The preferred reaction time is from about 15 minutes to about 60 minutes. Typically, a reaction time of about 30 minutes, e.g., from about 25 minutes to about 35 minutes, is employed.

At the end of a predetermined reaction time, the reaction mixture can be extracted directly for 2-hydroxyethidium or first processed to remove any insoluble particles from the mixture before the extraction. Any techniques that a skilled artisan is familiar with, such as filtration and centrifugation, can be used to remove insoluble particles. Furthermore, extracting 2-hydroxyethidium involves mature technologies such as those commonly used for extracting lipids and the like compounds that relatively more soluble in organic solvents than in water. Therefore, the 2-hydroxyethidium extraction can be readily accomplished by a skilled artisan. For example, a chloroform/methanol (2:1, volume/volume) system can be used to extract 2-hydroxyethidium from the reaction mixture. After mixing with the reaction mixture, the chloroform/methanol/reaction mixture can be separated into two phases: the upper phase of water and the lower phase of chloroform and methanol to which 2-hydroxyethidium is extracted. In a preferred embodiment, the reaction mixture is extracted at least 4 or 5 times. Finally, the organic solvent such as chloroform and methanol can be evaporated and a substantially purified 2-hydroxyethidium is obtained. When optimized, at least 80% or 90% of HE is converted to 2-hydroxyethidium by the method of the present invention. However, under conditions when the conversion rate is lower than 80% or a higher purity is desired, 2-hydroxyethidium in the extract can be further purified. The purification involves mature technology and can be readily accomplished by a skilled artisan. For example, a chloroform prewashed silica column can be used to purify 2-hydroxyethidium with methanol as the eluting solvent.

The starting materials employed in the method described here are relatively inexpensive, rendering the method a cost-effective method.

The practice of the present invention is further illustrated by the following non-limiting examples.

EXAMPLE 1

Superoxide Reacts with HE to Form a Characteristic Fluorescent Product that is Different from $E^+$ Materials and Methods Materials—Hydroethidine (dihydroethidium) was purchased from Molecular Probes Inc. (Eugene, Oreg., USA). Ethidium, DNA, ferricytochrome c, NADPH, L-arginine, xanthine, calcium chloride, potassium superoxide, diethylenetriamine pentaacetic acid (DTPA) were obtained from Sigma Chemical Co. (St. Louis, Mo., USA). The potassium superoxide in DMSO was prepared immediately prior to use as described in Lokesh, B. and Cunningham, M. *Toxicol. Lett.* 34:75–84, 1986. Bovine brain calmodulin was obtained from Calbiochem (San Diego, Calif., USA). Catalase was purchased from Boehringer Mannheim Co. (Sandhoferstrasse, Mannheim, Germany). Bovine copper, zinc superoxide dismutase and xanthine oxidase were purchased from Roche Molecular Biochemicals (Indianapolis, Ind., USA). 6-(R)-5,6,7,8-Tetrahydrobiopterin (6R—$BH_4$) was from Schircks (Iona, Switzerland) and 2-(N,N-diethylamino)-diazenolate-2-oxide (DEA/NO or DEA-NONOate) came from Alexis Biochemicals (San Diego, Calif., USA). DEA/NO stock solution (up to 20 mM in 0.01 M NaOH) was prepared immediately prior to use. Recombinant wild-type endothelial nitric oxide synthase (eNOS) was expressed in *Escherichia coli.* and purified as described in Vásquez-Vivar, J. et al. *Proc. Natl. Acad. Sci. USA* 95:9220–9225, 1998. The spin trap, 5-tert-butoxycarbonyl 5-methyl-1-pyrroline N-oxide (BMPO), was synthesized as described in Zhao, H. T. et al. *Free Radic. Biol. Med.* 31:599–606, 2001. Stock solutions of HE and $E^+$ (20 mM) were freshly prepared by dissolving in dimethyl sulfoxide and stored, protected from light, at −20° C. until use.

Xanthine oxidase (XO) activity—Xanthine oxidase was incubated with xanthine (1 mM) in phosphate buffer (100 mM, pH 7.4) containing DTPA (100 µM). Formation of uric acid was monitored at 296 nm using the extinction coefficient of 11,000 $M^{-1}cm^{-1}$, as described in Zhang, H. et al. *FEBS Lett.* 473:58–62, 2000.

Endothelial nitric oxide synthase activity—Endothelial nitric oxide synthase (NOS) activity was determined by quantifying the oxidation of oxyhemoglobin as described in Vásquez-Vivar, J. et al. *Biochem. J.* 362: 733–739, 2002. This assay consisted of calcium chloride (0.2 mM), calmodulin (20 µg/mL), glutathione (0.1 mM), bovine serum albumin (0.1 mg/mL), L-arginine (40 µM), $BH_4$ (10 µM), hemoglobin (approximately 8 µM), and DTPA (0.1 mM) in a HEPES buffer (50 mM, pH 7.4). Reactions were initiated by adding eNOS (2–4 µg protein), and changes in absorbance followed at 401 nm. Rates of nitric oxide formation were calculated from the linear portion of the readings for approximately 60 s, and the concentrations were calculated using an extinction coefficient of 38 $mM^{-1}$ $cm^{-1}$.

Superoxide production—Superoxide production was measured using the ferricytochrome c reduction assay ($\lambda$=550 nm, $\Delta\epsilon$=21,000 $M^{-1}$ $cm^{-1}$) as described in Messner, K. and Imlay, J. *Methods Enzymol.* 349:354–361, 2002. Rates of superoxide production by xanthine (1 mM) and xanthine oxidase (0.05 U/mL) were calculated from the reduction of ferricytochrome c (20 µM). Control incubations contained SOD (10 µg/mL).

Fluorescence measurements—The oxidation of HE in a superoxide generating system was performed on a Shimadzu RF-5301 PC spectrofluorometer (Shimadzu Scientific Instruments Inc., Japan). Typically, excitation was at 510 nm with a 3 or 5 nm slit width and the spectra were recorded over a wavelength region of 540–800 nm using a 10 or 20 nm slit width. The fluorescence emission spectra indicate the actual color of the product of superoxide and HE reaction, $E^+$ and HE.

HPLC analysis—HE, $E^+$ and HE/superoxide oxidation product were separated on an HPLC system equipped with fluorescence and UV detectors. The mobile phase was $H_2O/CH_3CN$. The stationary phase was a $C_{18}$ reverse phase column (Partisil ODS-3 250×4.5 mm, Alltech). Fluorescence detection at 510 nm (excitation) and 595 nm (emission) was used to monitor these compounds. Typically, 50 µL of sample was injected into the HPLC system (HP1100) with a $C_{18}$ column (250×4.5 mm) equilibrated with 10% $CH_3CN$ in 0.1% trifluoroacetic acid (TFA). HE, $E^+$ and HE/superoxide product were separated by a linear increase in $CH_3CN$ concentration from 10% to 40% in 30 min at a flow rate of 0.5 mL/min. The elution was monitored by a variable UV detector at 210 nm and 350 nm and a fluorescence detector with excitation at 510 nm and emission at 595 nm.

HPLC-mass spectrometry assay—Samples were analyzed by using LC-ESI-MS (Agilent 1100 LC/MSD, SL model). The samples (10 µL) were separated on a reverse phase $C_{18}$ column (Phenomenex, Jupiter, 250×2 mm, 5 µm, 100 Å) using water with 0.1% TFA and $CH_3CN$ with 0.1% TFA as a mobile phase at a flow rate of 0.2 mL/min. The mobile phase started at 10% $CH_3CN$ and linearly increased to 40% $CH_3CN$ in the first 40 min, to 55% $CH_3CN$ in the next 20 min and to 100% $CH_3CN$ in the final 10 min. Propionic acid/isopropanol (20:80, at a flow rate of 0.02 mL/min) was added post column for TFA fixing to improve the sensitivity. The drying gas flow was 12 L/min, drying gas temperature was 300° C., nebulizer pressure was 35 psig, vaporizer temperature was 325° C., capillary voltage was 3000 V, and fragmentor voltage was 90 V. Detection was made in the positive mode for the m/z range of 200–850.

Column chromatography—HE (50 µM) was incubated with X (1 mM) and XO (0.05 U/mL). The mixture was stirred several times in air. After 60 min, the mixture was extracted by chloroform until the chloroform phase was pale in color. The organic phase was concentrated, passed through a silica gel column (pre-washed by chloroform) and eluted with chloroform. After removing the residual HE, the column was eluted with methanol. Upon evaporation of the methanol, a red solid was obtained.

Results

Figure 2:
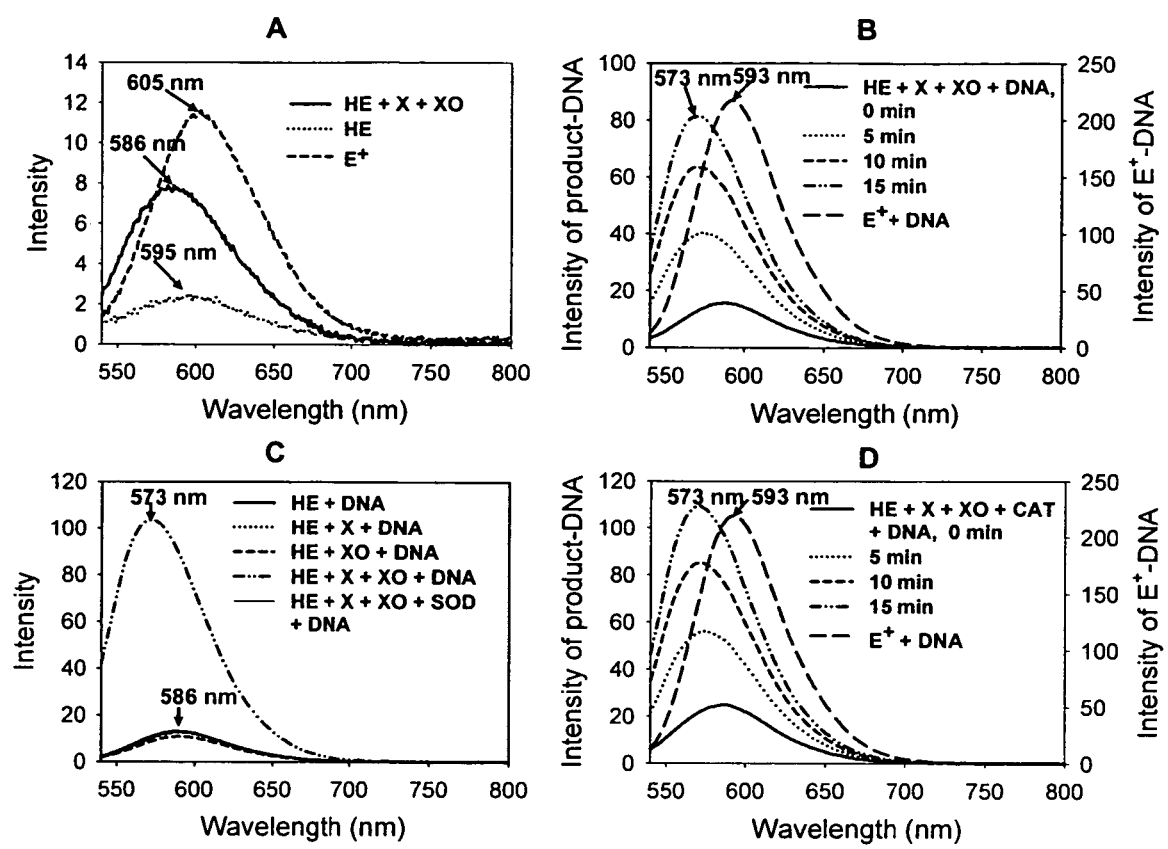
FIG. 2 shows time-dependent changes in fluorescence spectra of the product formed during oxidation of HE by xanthine/xanthine oxidase (X/XO). (A) Incubation mixtures consisted of HE (50 μM), xanthine (1 mM), DTPA (100 μM), and XO (0.05 U mL$^{-1}$) in aerated phosphate buffer (100 mM, pH 7.4). Reaction was initiated by the addition of XO and the fluorescence spectrum recorded after 30 min. Shown for comparison is the spectrum obtained from $E^+$ (50 μM) obtained under identical experimental conditions. (B) Same as (A) but in the presence of DNA (250 μg mL$^{-1}$). (C) Incubations contained HE (50 μM), DTPA (100 μM) and DNA (250 μg mL$^{-1}$) and xanthine (1 mM) or XO (0.05 U mL$^{-1}$), both in the presence and absence of SOD (20 μg mL$^{-1}$). (D) Same as (B) but in the presence of catalase (1000 U mL$^{-1}$).

Fluorescence spectra of the product formed from superoxide-dependent oxidation of HE—FIG. 2A shows the fluorescence spectra for HE (emission maximum=595 nm) (Table 1), the oxidation product of HE by X/XO (emission maximum=586 nm) and for ethidium (emission maximum=605 nm) in phosphate buffer. Superoxide generation was measured to be 8 µM/min. FIG. 2B shows the enhancement in the fluorescence intensity of the three compounds in the presence of DNA. DNA did not have any effect on the rate of oxidation of HE in this system (data not shown). Addition of superoxide dismutase (SOD) completely nullified the increase in fluorescence due to X/XO-catalyzed oxidation of HE (FIG. 2C). The fluorescence intensity of this product actually increased slightly in the presence of catalase (FIG. 2D). These results suggest that superoxide anion, but not $H_2O_2$ or $H_2O_2$-derived oxidant, is responsible for the formation of this product. As shown in FIG. 2B, the fluorescent spectrum of the product derived from the reaction between superoxide and HE is distinctly different from the $E^+$ fluorescence spectrum.

TABLE 1

Fluorescence spectral characteristics

| Fluorophores | Molecular weight[#] | Emission maximum (nm) | Retention time (min) | Extinction coefficient $(mM^{-1})$[*] | Fluorescence color |
|---|---|---|---|---|---|
| HE | 315.2 | 595 | 16 | 48 | Red |
| $E^+$ | 314.2 | 603 | 26.3 | 232 | Red |
| HE/superoxide product | 330.2 | 586 | 25.6 | 285 | Orange |
| HE/DNA | — | 585 | — | 260 | Red |
| $E^+$/DNA | — | 595 | — | 4750 | Red |
| HE/superoxide product/DNA | — | 567 | — | 5480 | Bright yellow |

[*]For $E^+$, excitation maximum = 518 nm, slit width = 3 nm and emission slit width = 20 nm. For HE/superoxide product, excitation maximum = 480 nm, slit width = 3 nm and emission slit width = 20 nm.
[#]The mass spectral detection was made in the positive mode and so m/z is 330. If the product takes a positive charge, m/z could be 329.

Figure 3:
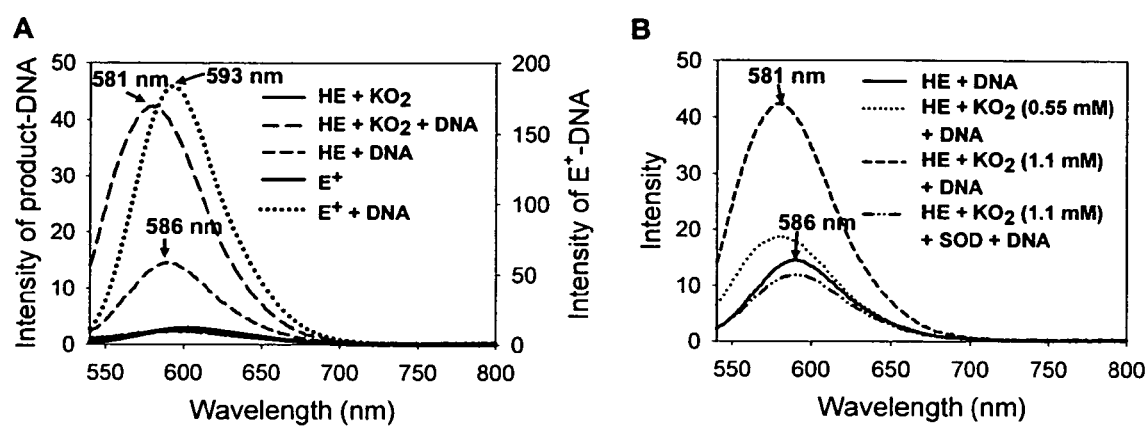
FIG. 3 shows fluorescence spectra of the product formed during oxidation of HE by potassium superoxide. (A) Incubations consisted of HE (50 μM), DTPA (100 μM), and KO$_2$ in the presence and absence of DNA (250 μg mL$^{-1}$) in phosphate buffer (100 mM, pH 7.4). Superoxide solution was prepared by adding 1 mg of KO$_2$ in 1 mL of dry DMSO and vortexed vigorously for 10 min. The reaction was initiated by adding 40 μL of freshly prepared KO$_2$ in DMSO to 0.46 mL of the above buffer (final concentration of KO$_2$ was 1.1 mM). (B) Same as (A) but also containing SOD (20 μg mL$^{-1}$). The extent of oxidation of HE under these conditions is much less than that observed in X/XO.

The addition of potassium superoxide ($KO_2$) in dimethyl sulfoxide to a mixture of HE, DNA and DTPA in phosphate buffer also produced a fluorescent product that is different from $E^+$ (FIG. 3A). The addition of SOD inhibited the formation of this product (FIG. 3B). Note that oxidation of HE by potassium superoxide is less than 50% of that observed in the X/XO system. This may be why the fluorescence emission maximum was detected at a higher wavelength during oxidation of HE by potassium superoxide.

Figure 4:
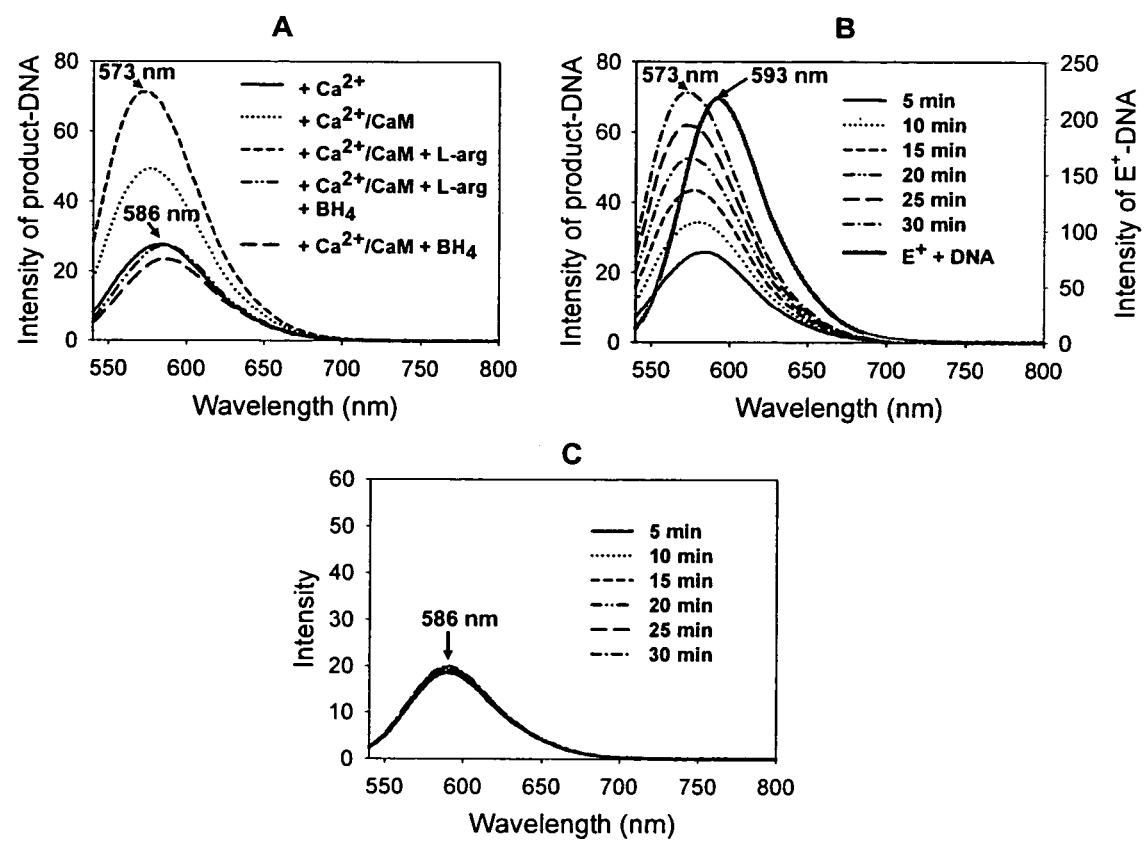
FIG. 4 shows fluorescence spectra of product formed from oxidation of HE by endothelial NOS. (A) Incubations consisted of NADPH (0.1 mM), DTPA (100 μM), HE (50 μM), L-arginine (0.1 mM), purified eNOS (6.25 μg mL$^{-1}$), and Ca$^{2+}$ (0.2 mM)/CaM (20 μg mL$^{-1}$) in a HEPES buffer (50 mM, pH 7.4). Spectra were obtained 30 min after the addition of eNOS to different incubation mixtures. There is little or no oxidation of HE in the presence of BH$_4$ (10 μM). (B) Time-dependent changes in fluorescence of the product formed from an incubation mixture containing NADPH (0.1 mM), HE (50 μM), DTPA (100 μM), Ca$^{2+}$ (0.2 mM)/CaM (20 μg mL$^{-1}$), and purified eNOS (6.25 μg mL$^{-1}$) in a HEPES buffer (50 mM, pH 7.4). (C) Same as (B) except in the presence of SOD (20 μg mL$^{-1}$).

It has been shown previously that endothelial nitric oxide synthase generates superoxide at the oxygenase domain in the absence of tetrahydrobiopterin ($BH_4$) (Vásquez-Vivar, J. et al. *Proc. Natl. Acad. Sci. USA* 95:9220–9225, 1998). FIG. 4A shows the spectral changes in fluorescence that occur during oxidation of HE by $BH_4$-free eNOS with active $Ca^{2+}$/CaM-dependent electron transfer from the reductase domain to the oxygenase domain. In the presence of $BH_4$, superoxide formation is inhibited; however, in the presence of L-arginine, $BH_4$ stimulates nitric oxide formation (Vásquez-Vivar, J. et al. *Biochem. J.* 362: 733–739, 2002). Oxidation of HE to the new product is inhibited when the enzyme is either reconstituted with $BH_4$ or under conditions facilitating nitric oxide formation. FIG. 4B describes the time-dependent changes in the fluorescence spectra derived from oxidation of HE by $BH_4$-free NOS in the presence of active $Ca^{2+}$/calmodulin. Inclusion of SOD in this incubation mixture inhibited the oxidation of HE (FIG. 4C).

Figure 5:
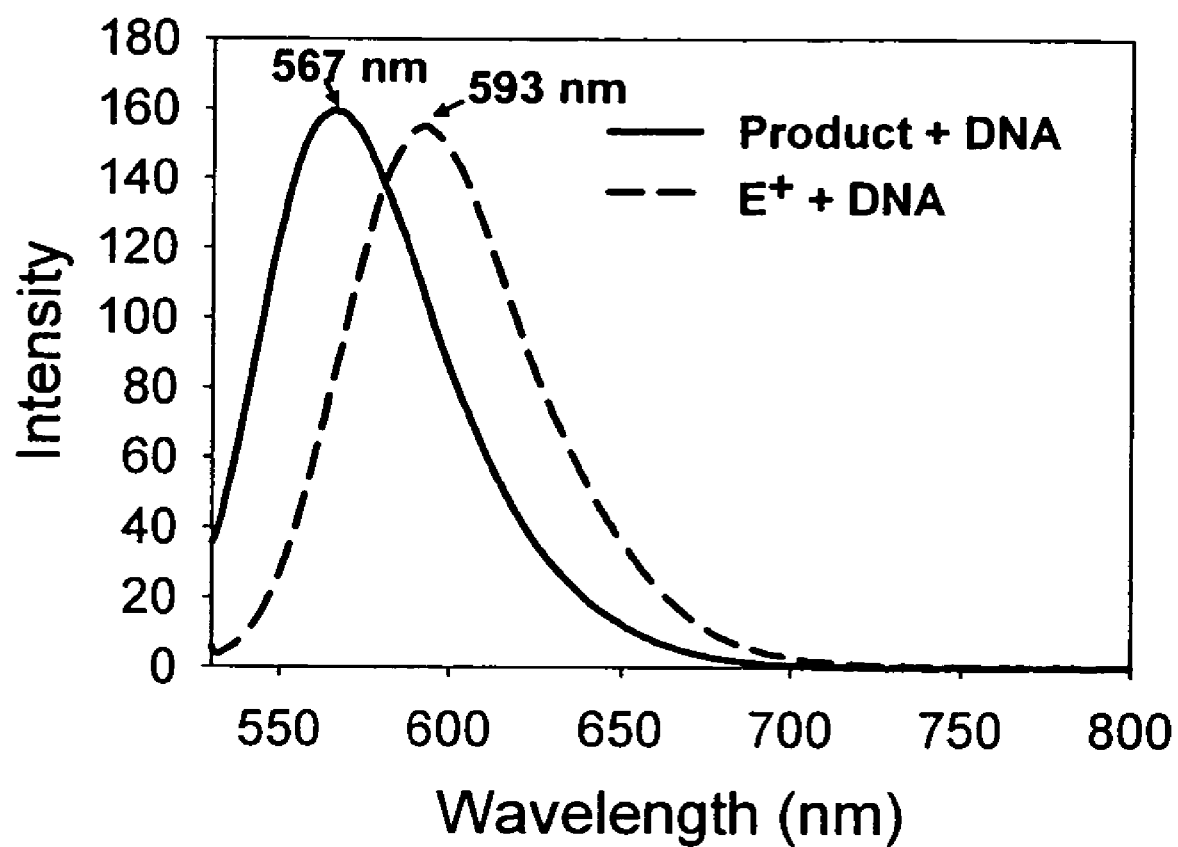
FIG. 5 shows fluorescence spectra of the purified product formed from oxidation of HE by X/XO and $E^+$ in the presence of DNA. Incubations contained 50 μM of the pure product, 50 μM E$^+$ and DNA (250 μg mL$^{-1}$) in phosphate buffer (100 mM, pH 7.4).

The oxidation product of HE obtained in the X/XO system was separated and purified by column chromatography. FIG. 5 shows the fluorescence spectrum of the purified product (emission maximum=567 nm) in the presence of DNA (250 µg mL$^{-1}$) in phosphate buffer. Using three different superoxide generating systems, it was shown that HE is oxidized to a fluorescent product that is different from $E^+$.

Figure 6:
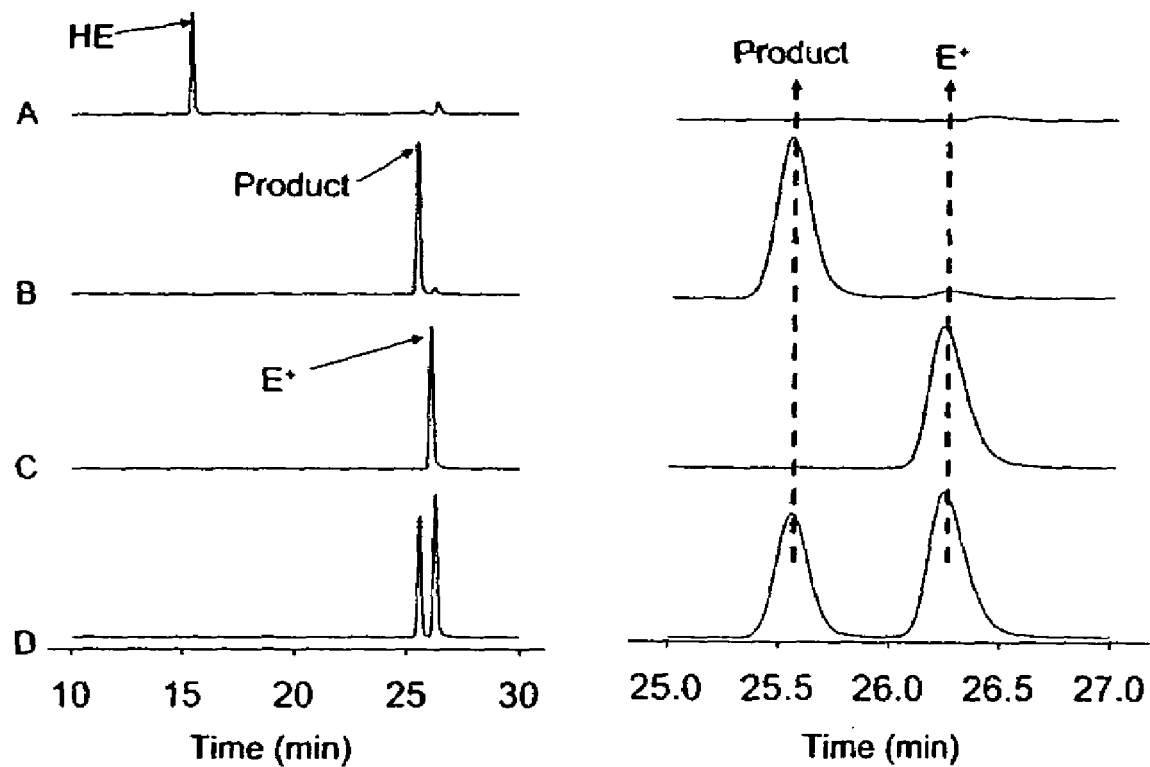
FIG. 6 shows HPLC chromatograms of HE, E$^+$ and the product formed from oxidation of HE by the X/XO system. (A) Incubations contained xanthine (1 mM), HE (50 μM), and DTPA (100 μM). (B) Same as above but in the presence of XO (0.05 U mL$^{-1}$). HPLC traces in (A) and (B) were obtained 30 min after starting the incubation. (C) HPLC trace of authentic E$^+$ (50 μM) in phosphate buffer (100 mM, pH 7.4). (D) Same incubation conditions as in (B) but spiked with authentic E$^+$ (50 μM). Right trace (A–D), HPLC chromatograms recorded on an expanded scale. Fluorescence detection at 510 nm (excitation) and 595 nm (emission) was used to monitor HE, E$^+$, and the oxidation product of HE.
Figure 7:
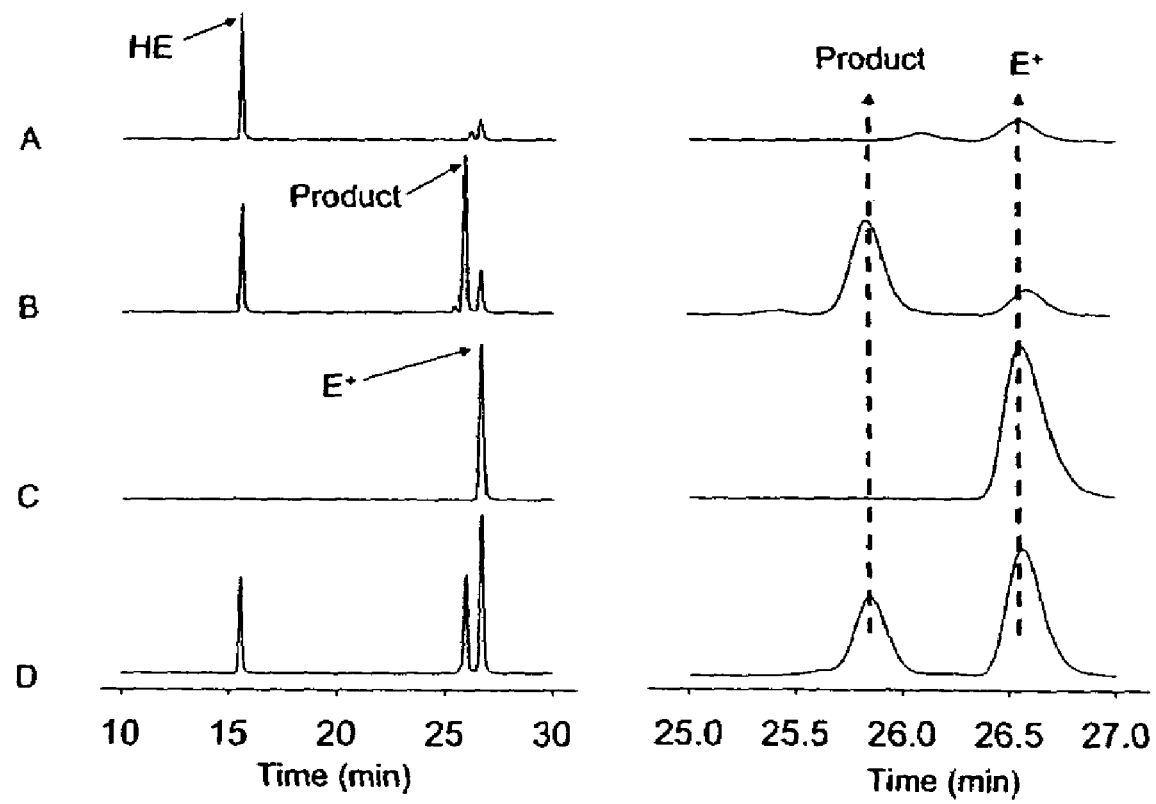
FIG. 7 shows HPLC chromatograms of potassium superoxide-induced oxidation of HE. (A) Incubations contained HE (50 μM) and DTPA (100 μM) in phosphate buffer (100 mM, pH 7.4). (B) Same as above except in the presence of $KO_2$ (1.1 mM). (C) HPLC trace of authentic E$^+$ (50 μM). (D) Same as (B) except the mixture also contained E$^+$ (25 μM). Right trace (A–D), HPLC chromatograms were recorded on an expanded scale. Fluorescence detection at 510 nm (excitation) and 595 nm (emission) was used to monitor HE, E$^+$, and the oxidation product of HE.

HPLC analysis of the oxidation product—The reaction product derived from oxidation of HE in a X/XO system was separated by HPLC with fluorescence detection. As shown in FIG. 6B, the product derived from superoxide-mediated oxidation of HE was eluted at a retention time of 25.6 min. In contrast, the retention time of $E^+$ under the same experimental conditions was 26.3 min (FIG. 6C). In the absence of XO, only HE was detected at a retention time of 16 min. When the incubation mixture containing HE, X and XO in phosphate buffer was spiked with $E^+$ and analyzed by HPLC, two different peaks (at 25.6 min and 26.3 min) were obtained. These results unambiguously demonstrate that the superoxide anion reacts with HE, forming a unique product that is distinctly different from $E^+$. Next, we verified that the same fluorescent product is formed from the reaction between HE and the superoxide anion generated from $K_2$. FIG. 7A shows the HPLC profile of HE, which consisted of a minor impurity peak due to $E^+$. This is expected, as HE is synthesized from a sodium borohydride reduction of $E^+$ (Lokesh, B. and Cunningham, M. *Toxicol. Lett.* 34:75–84, 1986). In the presence of $KO_2$ (1 mM) and HE, a new peak was observed (FIG. 7B). When the reaction mixtures containing HE and $KO_2$ were spiked with $E^+$, two separate HPLC peaks were detected (FIG. 7D).

Figure 8:
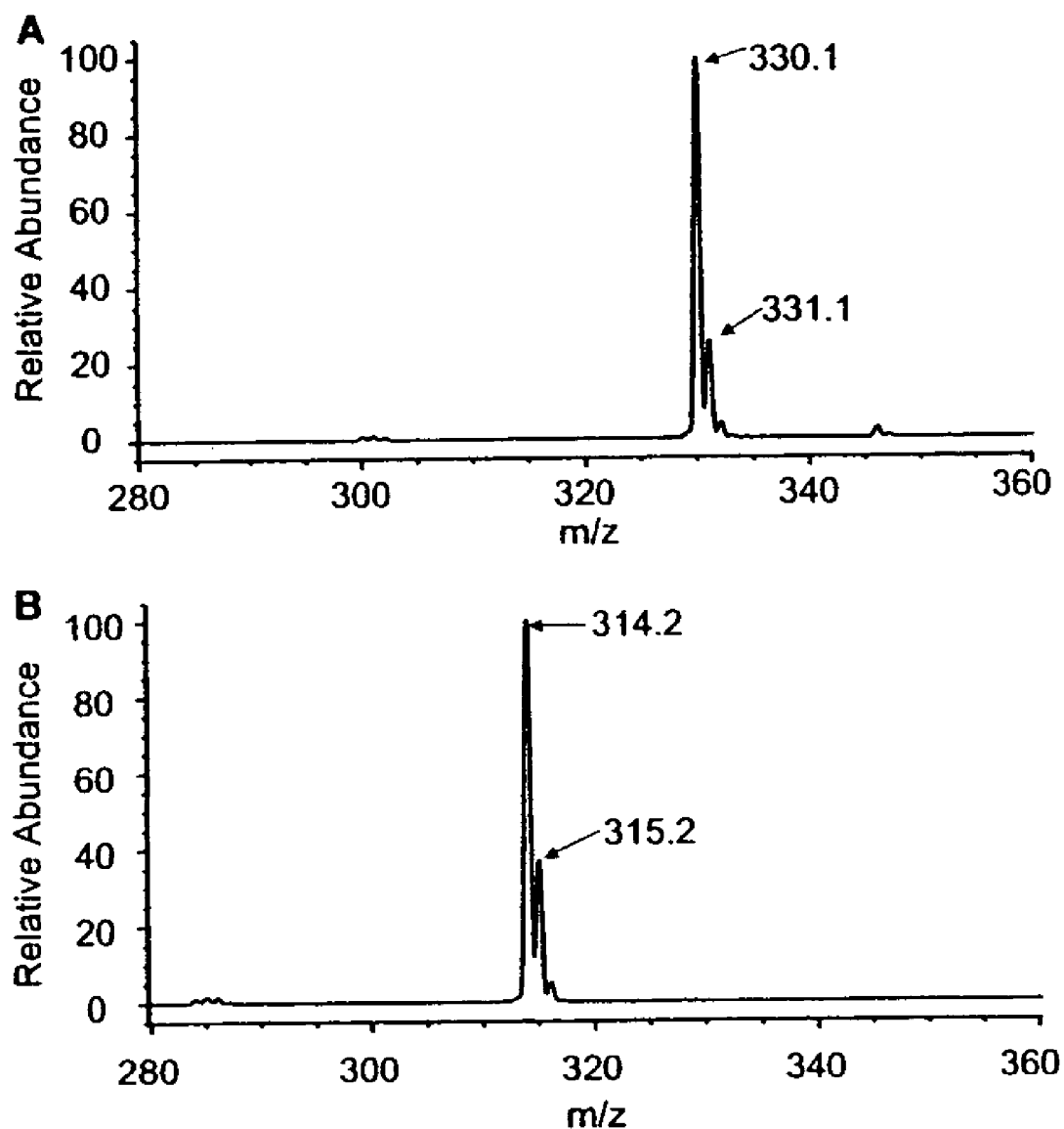
FIG. 8 shows HPLC-mass spectrometry. (A) The mass spectrum of new product taken from the LC peak at retention time of 34.30 min; incubations contained xanthine (1 mM), HE (50 μM), and DTPA (100 μM) and XO (0.05 U mL$^{-1}$) in phosphate buffer (100 mM, pH 7.4). (B) The mass spectrum of E$^+$ taken from the LC peak at retention time of 33.97 min; incubations contained E$^+$ (50 μM) in phosphate buffer (100 mM, pH 7.4).

HPLC-mass spectrometry—FIG. 8 shows the mass spectra of HE/superoxide and $E^+$. The molecular weight of the product of HE and superoxide is 330, but the molecular weight of $E^+$ is 314. These data indicate that HE reaction with superoxide does not form $E^+$ as a product.

DNA-gel electrophoresis—Samples from the incubation mixtures containing HE, xanthine, DTPA and xanthine oxidase in the presence of DNA were loaded onto a 1% agarose gel. In a control, experimental samples containing $E^+$ and DNA in phosphate buffer were included. The DNA gels was developed with UV light. We observed on the DNA gel that the color of the fluorescent product of HE/superoxide complexed with DNA is bright yellow and that of the DNA/$E^+$ complex is red.

Figure 9:
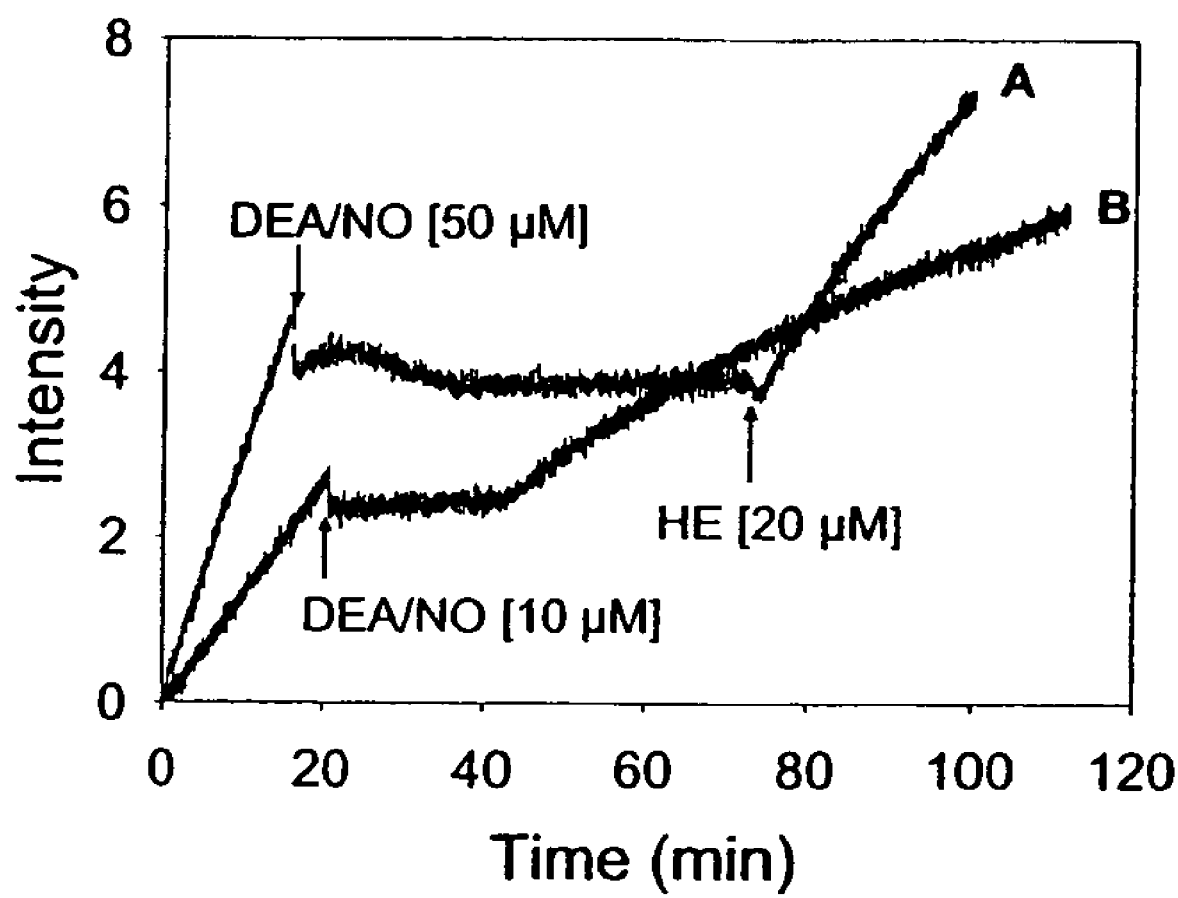
FIG. 9 shows the effect of DEA/NO on oxidation of HE by X/XO. (A) Incubation initially consisted of HE (50 μM), xanthine (1 mM), XO (0.025 U mL$^{-1}$) and DTPA (100 μM) in phosphate buffer (100 mM, pH 7.4). A 50 μM of DEA/NO added at the point indicated by downward arrow. After the increase in fluorescence intensity ceased, an additional bolus amount of HE was added. (B) Same as (A) except XO (0.005 U mL$^{-1}$) and DEA/NO were added at a much lower concentration (10 μM).

The effect of DEA/NO on the oxidation of HE by X/XO—FIG. 9 shows that the addition of DEA/NO initially inhibits the increase in fluorescence due to superoxide-dependent oxidation of HE in a X/XO system. At a low concentration of DEA/NO (10 µM), the increase of fluorescence due to superoxide-dependent oxidation of HE was inhibited (FIG. 9B). After DEA/NO decomposed, the fluorescence increased again, but at a low rate, as a significant portion of HE was oxidized by peroxynitrite. When more DEA/NO (50 µM) was added (FIG. 9A), peroxynitrite and/or other reactive nitrogen species generated by superoxide and DEA/NO completely oxidized the remaining HE in the system. Thus more HE was needed for sustaining the fluorescence due to the product of HE/superoxide reaction. During simultaneous generation of superoxide and nitric oxide (i.e., conditions favoring formation of peroxynitrite or other reactive nitrogen species), HE was not oxidized to the same fluorescent product. The addition of preformed peroxynitrite to an incubation containing HE (50 µM), DTPA (100 µM), and DNA in phosphate buffer (100 mM, pH 7.4) also did not generate the same fluorescent product obtained with superoxide (data not shown).

Kinetic analysis of the reaction between HE and superoxide—The rate constant between HE and superoxide was calculated from competition experiments. At saturating concentrations of HE, superoxide will be consumed as follows:

$$HE + O_2^{\bullet-} \xrightarrow{k_{HE}} \text{Fluorescent product (P)}$$
$$\text{Scavenger} + O_2^{\bullet-} \xrightarrow{k_{scavenger}} \text{Product}$$

Dismutation of superoxide was not considered in our analysis, because at saturating concentrations of HE (compared to superoxide flux), this reaction is negligible (Vásquez-Vivar, J. et al. *Free Radic. Biol. Med.* 31:975–985, 2001). Thus, assuming a steady-state approximation, the rate of superoxide consumption will be equal to new fluorescent product (P) formation, defined by $$-\frac{d[O_2^-]}{dt} = k_{HE}[HE][O_2^-] + k_{scavenger}[\text{scavenger}][O_2^-]$$

where $k_{HE}$ is the apparent rate constant for the reaction of HE with superoxide under the experimental conditions. Therefore, the ratio between V and $V_0$ that corresponds to the rate of new product formation in the presence and absence of scavenger, respectively, is defined by $$\frac{V_0}{V} = \frac{d[O_2^-]/dt}{d[P]/dt} = 1 + \frac{k_{scavenger}[\text{scavenger}]}{k_{HE}[HE]}$$

The values of V and $V_0$ can be calculated from variations in fluorescence intensity of new product over time. In these experiments, 5-tert-butoxycarbonyl 5-methyl-1-pyrroline N-oxide (BMPO) and bovine Cu, Zn-SOD were used to trap or dismutate superoxide. The rate constant used for the reaction between BMPO and superoxide was 77±5 M$^{-1}$ s$^{-1}$ (Rosen, G. et al. *J. Biol. Chem.* 277:40275–40280, 2002) and 3×10$^9$ M$^{-1}$ s$^{-1}$ for Cu, Zn-SOD.

Using the competition kinetic analysis described above, the tentative rate constant between the superoxide anion and HE is estimated to be approximately 2.6±0.6×10$^5$ M$^{-1}$ s$^{-1}$.

In summary, this example demonstrates that superoxide reacts with HE to form a characteristic fluorescent product that is different from $E^+$. In the presence of other reactive oxygen and nitrogen species (e. g., hydrogen peroxide, hydroxyl radical or peroxynitrite), HE was not oxidized to form the same fluorescent product.

EXAMPLE 2

Figure 10:
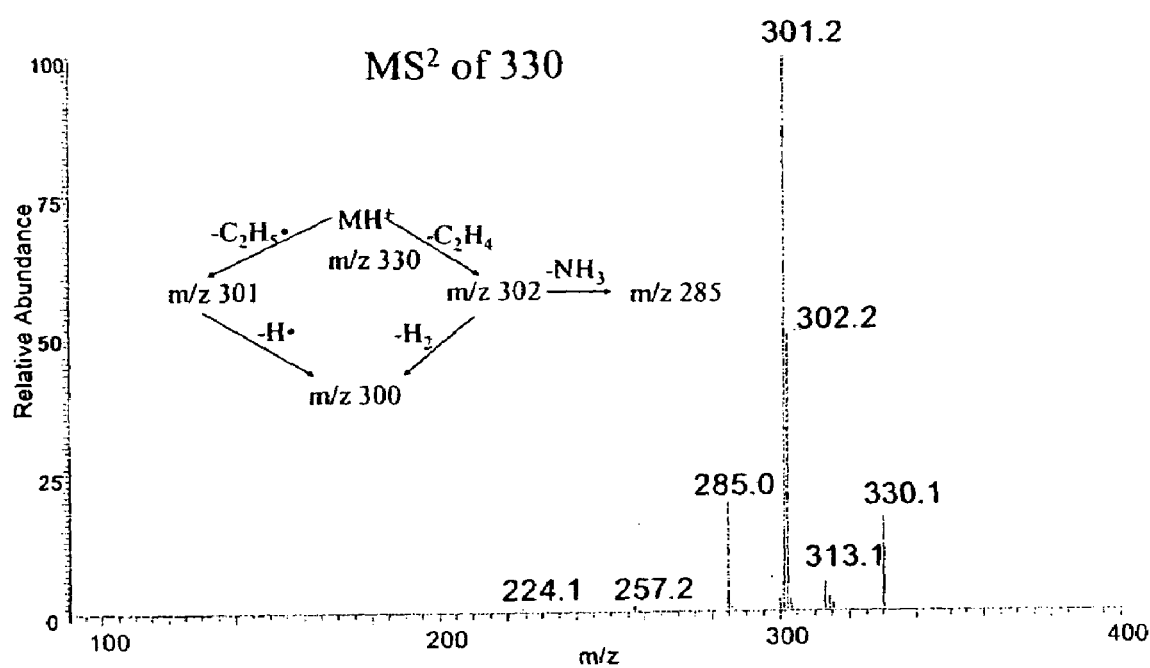
FIG. 10 shows the mass spectral fragmentation pattern of the reaction product of HE and superoxide.

Identification of the Reaction Product between Superoxide and HE as 2-Hydroxyethidium We identified the structure of the product formed from the reaction between superoxide and HE as 2-hydroxyethidium. An LCQ Classic ion trap instrument and a Varian XL-300 300 MHz NMR machine were used for the identification. Solutions of 0.1% formic acid in acetonitrile were electrosprayed at 2.5 Kv. The capillary temperature was 190° C. Mass spectral fragmentation pattern (FIG. 10) shows that the oxygen atom is attached to the ring and the MS/MS pattern is consistent with the 2-hydroxyethidium structure. Fragmentation pattern showed that after losing an ethylene group, a 17 mass unit loss (OH) was detected as opposed to the 16 mass unit loss of $NH_2$ seen with the ethidium fragmentation.

Figure 11:
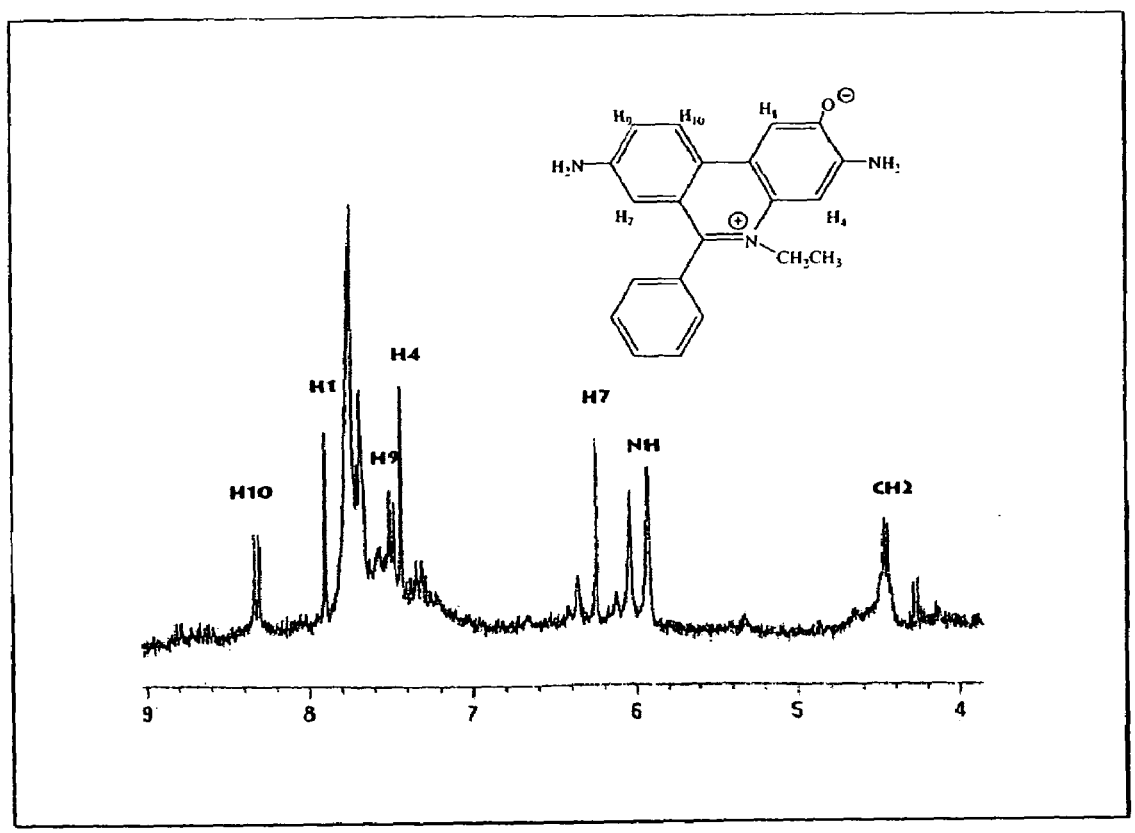
FIG. 11 shows the NMR spectrum (aromatic region) of the reaction product of HE and superoxide.

The NMR spectrum was obtained in deuterated DMSO and an expansion of the aromatic region is shown in FIG. 11 (accumulation time, 2 seconds). The chemical shifts (in ppm) of the product are: (H1, 7.88; H2, –; H4, 7.42; H7, 6.24; H9, 7.48; H10, 8.32). Decoupling experimental data (in Hz) are as follows: (J7,9=2.4; J9,10=8.99). These effects are as expected from the addition of an oxygen atom at the 2-position. These are consistent with the proposed structure in FIG. 11.

EXAMPLE 3

Synthesis of 2-Hydroxyethidium

2-Hydroxyethidium was synthesized as follows: Fremy's salt was dissolved in a solution containing acetonitrile and phosphate buffer (pH, 7.4, 10 mM) in a 1:1 ratio. Fremy's salt solution (4.5 equivalents) was slowly added to HE (60 μM) in 0.1 M phosphate buffer under stirring. This mixture was stirred gently for 30 minutes. The reaction mixture was filtered and extracted with a 2:1 chloroform and methanol mixture 4–5 times. The product was purified in a Silica column that was prewashed with chloroform. The trace amounts of HE can be removed by using chloroform as an eluting solvent. Then the product was washed out using methanol as an eluting solvent. The typical column used was 50 cm in length with 35–40 cm silica gel filled. The diameter of the column was dependent on the amount of reactive mixture. The excess solvent was removed by vacuum. This procedure gave a 90% yield (90% of HE was converted to 2-hydroxyethidium). The purity of product was >95% (HPLC analysis).

EXAMPLE 4

Figure 12:
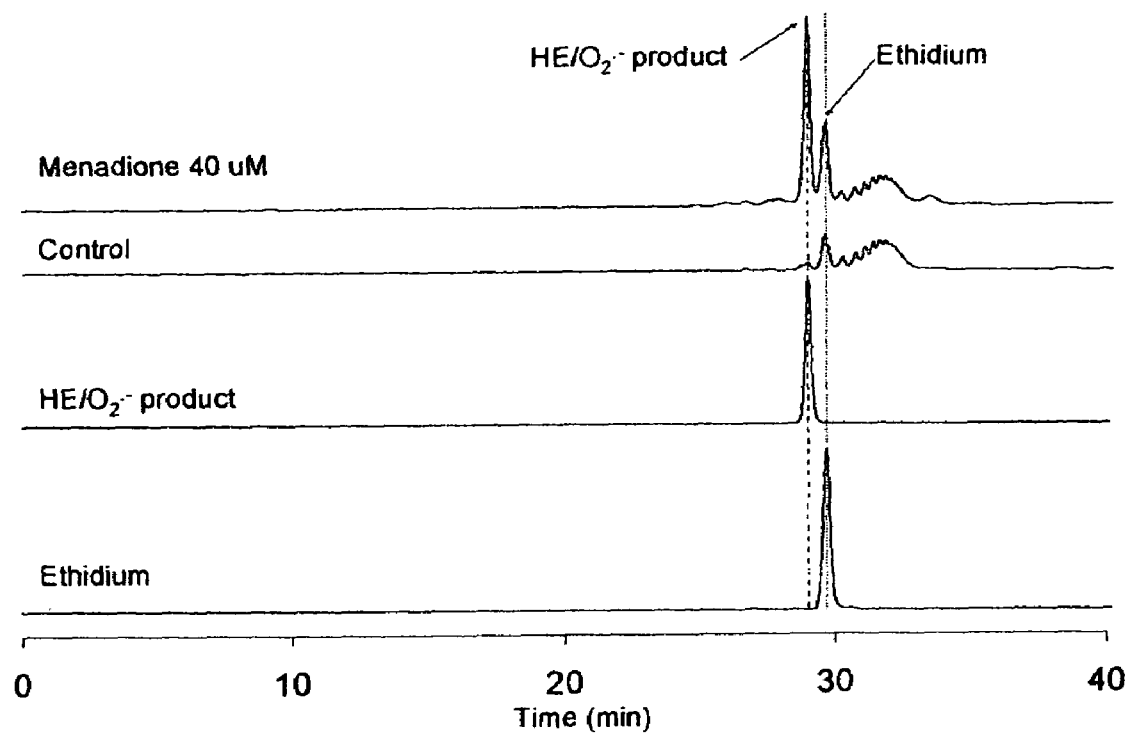
FIG. 12 shows HPLC trace of control cells and cells treated with 40 μM menadione.

Intracellular Detection and Quantitation of Superoxide Using 2-Hydroxyethidium as the Standard Bovine aortic endothelial cells were treated with menadione, a redox-cycling quinone known to induce cellular oxidative stress. After 25 min of exposure, cells were washed free of extracellular menadione and treated with 10 μM of HE for 20 min. Cells were washed and fluorescent images obtained in a fluorescence microscope. We observed that menadione-treated cells but not control cells showed intense red fluorescence. Cells were lysed and products extracted with n-butanol. After centrifugation to separate out the cell debris, the top layer of butanol was dried, dissolved in water, and HPLC/fluorescence chromatogram was obtained (FIG. 12). The intense peak eluting at 29 min corresponds to that of 2-hydroxyethidium (FIG. 12, top trace). For better separation in biological samples, a linear increase in $CH_3CN$ concentration from 10% to 70% in 46 min was used instead of a linear increase in $CH_3CN$ concentration from 10% to 40% in 30 min. The other HPLC analysis conditions were same as described above.

The present invention is not intended to be limited to the foregoing examples, but to encompass all such modifications and variations as come within the scope of the appended claims.

We claim:

1. Substantially purified 2-hydroxyethidium wherein the 2-hydroxyethidium is at least 80% pure.

2. The substantially purified 2-hydroxyethidium of claim 1 wherein the 2-hydroxyethidium is at least 85% pure.

3. The substantially purified 2-hydroxyethidium of claim 1 wherein the 2-hydroxyethidium is at least 90% pure.

4. The substantially purified 2-hydroxyethidium of claim 1 wherein the 2-hydroxyethidium is at least 95% pure.

5. The substantially purified 2-hydroxyethidium of claim 1 wherein the 2-hydroxyethidium is at least 99% pure.

6. A method for detecting superoxide in a sample comprising the steps of:
    adding hydroethidine to the sample;
    subjecting the sample to conditions under which hydroethidine and superoxide can react to generate 2-hydroxyethidium; and
    detecting specifically the presence of 2-hydroxyethidium in the sample wherein the presence of 2-hydroxyethidium indicates the presence of superoxide in the sample.

7. The method of claim 6, wherein the sample is a biological sample.

8. The method of claim 6, wherein the presence of 2-hydroxyethidium is detected by HPLC.

9. A method for determining the amount of superoxide in a sample comprising the steps of:
    adding hydroethidine to the sample;
    subjecting the sample to conditions under which hydroethidine and superoxide can react to generate 2-hydroxyethidium; and
    measuring specifically the amount of 2-hydroxyethidium in the sample for determining the amount of superoxide in the sample.

10. The method of claim 9, wherein the sample is a biological sample.

11. The method of claim 9, wherein the amount of 2-hydroxyethidium is measured by HPLC.

12. The method of claim 9, wherein the amount of 2-hydroxyethidium is measured by HPLC-mass spectrometry.

13. A method for producing 2-hydroxyethidium comprising the steps of:
    dissolving Fremy's salt in a first solution containing acetonitrile and phosphate buffer to form a Fremy's salt solution;
    mixing the Fremy's salt solution with a second solution containing hydroethidine and phosphate buffer to form a reaction mixture in which 2-hydroxyethidium is generated;
    extracting 2-hydroxyethidium from the reaction mixture; and
    obtaining substantially purified 2-hydroxyethidium from the extract.

14. The method of claim 13, wherein more than 80% of hydroethidine is converted to 2-hydroxyethidium.

15. The method of claim 13, wherein more than 90% of hydroethidine is converted to 2-hydroxyethidium.

16. The method of claim 13, wherein the volume ratio of acetonitrile to phosphate buffer in the first solution is about 1 to 1, and the phosphate buffer is of about 10 mM to about 50 mM and has a pH value from about 7.4 to about 7.6.

17. The method of claim 13, wherein the concentration of hydroethidine in the second solution is from about 60 μM to about 120 μM, and the phosphate buffer of the second solution is of about 50 mM to about 100 mM and has a pH value from about 7.4 to about 7.6.

18. The method of claim 13, wherein the molar ratio of Fremy's salt to hydroethidine in the reaction mixture is about 4.5 to 1.

19. The method of claim 13, wherein the Fremy's salt solution and the second solution containing hydroethidine and phosphate buffer are mixed for about 15 minutes to about 60 minutes.

20. The method of claim 19, wherein the Fremy's salt solution and the second solution containing hydroethidine and phosphate buffer are mixed for about 25 minutes to about 35 minutes.

21. The method of claim 13, wherein an extraction solution containing chloroform and methanol is used to extract 2-hydroxyethidium from the reaction mixture.

22. The method of claim 21, wherein the volume ratio of chloroform to methanol in the extraction solution is from about 1.8 to 1.0 to about 2.2 to 1.0.

23. The method of claim 13, wherein substantially purified 2-hydroxyethidium is obtained by using a silica column to purify 2-hydroxyethidium from the extract.

24. The method of claim 13, wherein the method further comprises separating insoluble matters, if any, from the reaction mixture before the reaction mixture is extracted for 2-hydroxyethidium.

25. A method for producing substantially purified 2-hydroxyethidium comprising the steps of:

mixing superoxide and hydroethidine under conditions that superoxide and hydroethidine react to form 2-hydroxyethidium; and purifying 2-hydroxyethidium to obtain substantially purified 2-hydroxyethidium.

* * * * *